US012721520B2

(12) United States Patent
Hu et al.

(10) Patent No.: US 12,721,520 B2
(45) **Date of Patent: *Sep. 1, 2026**

(54) META-OPTICS-BASED SYSTEMS AND METHODS FOR OCULAR APPLICATIONS

(71) Applicant: Massachusetts Institute of Technology, Cambridge, MA (US)

(72) Inventors: Juejun Hu, Newton, MA (US); Tian Gu, Fairfax, VA (US); Mikhail Shalaginov, Somerville, MA (US); Fan Yang, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 210 days.

This patent is subject to a terminal disclaimer.

(21) Appl. No.: 18/540,256

(22) Filed: Dec. 14, 2023

(65) Prior Publication Data

US 2024/0122473 A1 Apr. 18, 2024

Related U.S. Application Data

(63) Continuation of application No. 17/556,884, filed on Dec. 20, 2021, now Pat. No. 11,850,001, which is a (Continued)

(51) Int. Cl.
*A61B 3/14* (2006.01)
*A61B 3/12* (2006.01)
(Continued)

(52) U.S. Cl.
CPC .................. *A61B 3/14* (2013.01); *A61B 3/12* (2013.01); *G02B 1/002* (2013.01);
(Continued)

(58) Field of Classification Search
CPC .. A61B 3/14; A61B 3/12; A61B 3/113; G02B 1/002; G02B 27/0093;
(Continued)

(56) References Cited

U.S. PATENT DOCUMENTS 3,085,469 A 4/1963 Carlson
4,061,423 A 12/1977 Pomerantzeff
(Continued)

FOREIGN PATENT DOCUMENTS

CN 107533362 A 1/2018
CN 108882845 A 11/2018
(Continued)

OTHER PUBLICATIONS

A Comprehensive List of 3D Sensors Commonly Leveraged in ROS Development. ROS-Industrial. Accessed at https://rosindustrial.org/3d-camera-survey on Sep. 12, 2019, 11 pages.
(Continued)

*Primary Examiner* — Mohammed A Hasan
(74) *Attorney, Agent, or Firm* — Smith Baluch LLP

(57) ABSTRACT

Meta-lens based ocular imaging, near-eye display, and eye-tracking systems are described. The systems can include a single focusing optic and an integrated circuit that provides illumination light and includes an imaging array. The focusing optic includes meta-atoms formed on a substrate. The systems may have no moving parts and achieve imaging or image-projection fields-of-view approaching or exceeding 180 degrees. Because of their low part count, the systems can be robust and have a very small form factor.

20 Claims, 8 Drawing Sheets

Related U.S. Application Data continuation of application No. 17/164,425, filed on Feb. 1, 2021, now Pat. No. 11,206,978.

(60) Provisional application No. 63/003,782, filed on Apr. 1, 2020.

(51) Int. Cl.

| | |
|---|---|
| ***G02B 1/00*** | (2006.01) |
| ***G02B 27/00*** | (2006.01) |
| ***G02B 27/01*** | (2006.01) |
| ***G06F 3/01*** | (2006.01) |
| *A61B 3/113* | (2006.01) |

(52) U.S. Cl.
CPC ..... *G02B 27/0093* (2013.01); *G02B 27/0172* (2013.01); *G06F 3/013* (2013.01); *A61B 3/113* (2013.01); *G02B 2027/0123* (2013.01); *G02B 2027/0147* (2013.01)

(58) Field of Classification Search
CPC ........ G02B 27/0172; G02B 2027/0123; G02B 2027/0147; G06F 3/013
USPC .......................................................... 351/206
See application file for complete search history.

(56) References Cited

U.S. PATENT DOCUMENTS

| | | | | |
|---|---|---|---|---|
| 9,295,388 | B2 | 3/2016 | Lawson et al. | |
| 10,408,416 | B2 | 9/2019 | Khorasaninejad et al. | |
| 10,408,419 | B2 | 9/2019 | Aieta et al. | |
| 10,591,643 | B2 | 3/2020 | Lin et al. | |
| 10,591,746 | B2 | 3/2020 | Macinnis | |
| 10,979,635 | B2 | 4/2021 | Hu et al. | |
| 11,206,978 | B2 | 12/2021 | Hu et al. | |
| 11,850,001 | B2 * | 12/2023 | Hu | G06F 3/013 |
| 2013/0057828 | A1 | 3/2013 | De | |
| 2013/0091515 | A1 * | 4/2013 | Sakata | H04N 17/04 725/10 |
| 2015/0131050 | A1 * | 5/2015 | Bublitz | A61B 3/12 351/246 |
| 2015/0289762 | A1 | 10/2015 | Popovich et al. | |
| 2016/0296112 | A1 | 10/2016 | Fletcher et al. | |
| 2017/0010466 | A1 | 1/2017 | Klug et al. | |
| 2017/0082263 | A1 | 3/2017 | Byrnes et al. | |
| 2017/0109562 | A1 | 4/2017 | Shroff et al. | |
| 2017/0307857 | A1 | 10/2017 | Ning | |
| 2018/0275409 | A1 * | 9/2018 | Gao | H04N 13/383 |
| 2019/0044003 | A1 | 2/2019 | Heck et al. | |
| 2019/0049632 | A1 | 2/2019 | Shin et al. | |
| 2019/0113775 | A1 | 4/2019 | Jang et al. | |
| 2019/0196068 | A1 | 6/2019 | Tsai et al. | |
| 2019/0369401 | A1 * | 12/2019 | Rolland | G02B 27/0176 |
| 2020/0081294 | A1 | 3/2020 | You et al. | |
| 2020/0241301 | A1 | 7/2020 | Basset | |
| 2020/0400943 | A1 * | 12/2020 | Kessler | G02B 27/283 |
| 2021/0003900 | A1 | 1/2021 | Chen | |
| 2021/0306564 | A1 | 9/2021 | Hu et al. | |
| 2024/0337850 | A1 * | 10/2024 | Gao | H04N 13/344 |

FOREIGN PATENT DOCUMENTS

| | | | |
|---|---|---|---|
| CN | 110891533 | A | 3/2020 |
| WO | 2018204856 | A1 | 11/2018 |
| WO | 2019006076 | A1 | 1/2019 |
| WO | 2019119025 | A1 | 6/2019 |
| WO | 2019148200 | A1 | 8/2019 |
| WO | 2019165620 | A1 | 9/2019 |

OTHER PUBLICATIONS

Aieta et al., "Aberration-free ultrathin flat lenses and axicons at telecom wavelengths based on plasmonic metasurfaces." Nano letters 12.9 (2012): 4932-4936.

Aieta et al., "Aberrations of flat lenses and aplanatic metasurfaces." Optics express 21.25 (2013): 31530-31539.

Alu et al., Honorary issue for Federico Capasso on "Metamaterials & Metasurfaces". Nanophotonics 7, (2018). 311 pages.

An et al., "A Novel Modeling Approach for All-Dielectric Metasurfaces Using Deep Neural Networks." arXiv preprint arXiv:1906.03387 (2019). 18 pages.

An et al., "Generative Multi-Functional Meta-Atom and Metasurface Design Networks." arXiv preprint arXiv:1908.04851 (2019). 17 pages.

Arbabi et al., "Miniature optical planar camera based on a wide-angle metasurface doublet corrected for monochromatic aberrations." Nature communications 7.1 (2016): 1-9.

Arbabi et al., "Multiwavelength metasurfaces through spatial multiplexing." Scientific reports 6 (2016): 32803. 8 pages.

Capasso, "The future and promise of flat optics: a personal perspective." Nanophotonics 7.6 (2018): 953-957.

Chen et al., "A broadband achromatic metalens for focusing and imaging in the visible." Nature nanotechnology13.3 (2018): 220-226.

Dehoog et al., "Fundus camera systems: a comparative analysis." Applied optics 48.2 (2009): 221-228.

Du et al., "Stencil lithography for scalable micro-and nanomanufacturing." Micromachines 8.4 (2017): 131, 24 pages.

Engelberg et al., "Near-IR wide-field-of-view Huygens metalens for outdoor imaging applications." Nanophotonics 9.2 (2020): 361-370.

Eye Tracking Market worth $1,786 million by 2025. Markets and Markets. Accessed at https://www.marketsandmarkets.com/PressReleases/eye-tracking.asp on Sep. 11, 2020. 5 pages.

Fierson et al., "Telemedicine for evaluation of retinopathy of prematurity." Pediatrics 135.1 (2015): e238-e254. 19 pages.

Genevet et al., "Recent advances in planar optics: from plasmonic to dielectric metasurfaces." Optica 4.1 (2017): 139-152.

Gissibl et al., "Two-photon direct laser writing of ultracompact multi-lens objectives." Nature Photonics 10.8 (2016): 554-560.

Groever et al., "Meta-lens doublet in the visible region." Nano letters 17.8 (2017): 4902-4907.

Grunnet-Jepsen et al., "Best-Known-Methods for Tuning Intel® RealSense™ D400 Depth Cameras for Best Performance." Intel Corporation: Satan Clara, CA, USA 1 (2018). 10 pages.

Heaney, Hololens 2's Field of View Revealed. UploadVR Feb. 25, 2019. Accessed at https://uploadvr.com/hololens-2-field-of-view/ on Aug. 20, 2019, 10 pages.

Hu et al., "Demonstration of a-Si metalenses on a 12-inch glass wafer by CMOS-compatible technology." arXiv preprint arXiv:1906.11764 (2019). 6 pages.

International Search Report and Written Opinion in International Patent Application No. PCT/US2021/016064 mailed May 6, 2021, 10 pages.

JDC Micro LED Start Kit. Jasper Display Corp. Accessed at https://www.jasperdisplay.com/products/micro-led-start-kit/ on Aug. 20, 2019, 3 pages.

Kamali et al., "A review of dielectric optical metasurfaces for wavefront control." Nanophotonics 7.6 (2018): 1041-1068.

Kamali et al., "Decoupling optical function and geometrical form using conformal flexible dielectric metasurfaces." Nature communications 7.1 (2016): 1-7.

Kar et al., "A review and analysis of eye-gaze estimation systems, algorithms and performance evaluation methods in consumer platforms." IEEE Access 5 (2017): 16495-16519.

Kerker et al., "Electromagnetic scattering by magnetic spheres." JOSA 73.6 (1983): 765-767.

Khorasaninejad et al., "Metalenses at visible wavelengths: Diffraction-limited focusing and subwavelength resolution imaging." Science 352.6290 (2016): 1190-1194.

Khorasaninejad et al., "Metalenses: Versatile multifunctional photonic components." Science 358.6367 (2017): eaam8100. 10 pages.

(56) References Cited

OTHER PUBLICATIONS

Kress et al., "A review of head-mounted displays (HMD) technologies and applications for consumer electronics." Photonic Applications for Aerospace, Commercial, and Harsh Environments IV. vol. 8720. International Society for Optics and Photonics, May 31, 2013. 14 pages.
Kuznetsov et al., "Optically resonant dielectric nanostructures." Science 354.6314 (2016): aag2472. 10 pages.
Lalanne et al., "Blazed binary subwavelength gratings with efficiencies larger than those of conventional échelette gratings." Optics letters 23.14 (1998): 1081-1083.
Lalanne et al., "Metalenses at visible wavelengths: past, present, perspectives." Laser & Photonics Reviews 11.3 (2017): 1600295. 11 pages.
Lee et al., Metasurface eyepiece for augmented reality. Nat Commun 9, 4562 (2018). https://doi.org/10.1038/s41467-018-07011-5. 10 pages.
Li et al. "Metalens-based miniaturized optical systems." Micromachines 10.5 (2019): 310, 21 pages.
Maguid et al., "Photonic spin-controlled multifunctional shared-aperture antenna array." Science 352.6290 (2016): 1202-1206.
Metalenz Inc. Accessed at https://www.metalenz.com/ on Apr. 29, 2020. 2 pages.
Monochromatic 2.5-um pitch (10K DPI) 1080P MicroLED Display. Jade Bird Display. Accessed at https://www.jb-display.com/2-5-um-pitch on Sep. 12, 2019, 1 page.
Nagiel et al., "Ultra-widefield fundus imaging: a review of clinical applications and future trends." Retina 36.4 (2016): 660-678.
Optos Products. Accessed at https://www.optos.com/en/products/ on Sep. 11, 2020. 27 pages.
Panwar et al., "Fundus photography in the 21st century—a review of recent technological advances and their implications for worldwide healthcare." Telemedicine and e-Health 22.3 (2016): 198-208.
Patel et al., "Ultra-widefield retinal imaging: an update on recent advances." Therapeutic Advances in Ophthalmology 12 (2020): 2515841419899495. 12 pages.
Pe'Er et al., "Measurement of choroidal melanoma basal diameter by wide-angle digital fundus camera: a comparison with ultrasound measurement." Ophthalmologica 220.3 (2006): 194-197.
Pugh et al., "Screening for diabetic retinopathy: the wide-angle retinal camera." Diabetes care 16.6 (1993): 889-895.
Shalaginov et al., "A single-layer panoramic metalens with> 170 {\deg} diffraction-limited field of view." arXiv preprint arXiv:1908.03626 (2019). 14 pages.
Shalaginov et al., "High-index-contrast dielectric metasurface optics for MWIR imaging (Conference Presentation)." Advanced Optics for Imaging Applications: UV through LWIR IV. vol. 10998. International Society for Optics and Photonics, 2019. 11 pages.
Shrestha et al., "Broadband achromatic dielectric metalenses." Light: Science & Applications 7.1 (2018): 1-11.
Staurenghi et al., "Scanning laser ophthalmoscopy and angiography with a wide-field contact lens system." Archives of Ophthalmology 123.2 (2005): 244-252.
Structured Light Took Kit. GitHub. Accessed at https://github.com/jhdewitt/sltk; first commit on Feb. 28, 2017; latest commit on Apr. 4, 2018, 5 pages.
Toslak et al., "Near-infrared light-guided miniaturized indirect ophthalmoscopy for nonmydriatic wide-field fundus photography." Optics letters 43.11 (2018): 2551-2554.
Toslak et al., "Trans-palpebral illumination: an approach for wide-angle fundus photography without the need for pupil dilation." Optics letters 41.12 (2016): 2688-2691.
Toslak et al., Trans-pars-planar illumination enables a 200° ultra-wide field pediatric fundus camera for easy examination of the retina. Biomedical Optics Express 11.1 (2020): 68-76.
Tseng et al., Metalenses: Advances and Applications. Adv. Opt. Mater. 6, 1-16 (2018). 16 pages.
Ultra-Wide Field Retinal Imaging Device. Nikon. Accessed at https://www.nikon.com/about/technology/product/retinal-imaging/index.htm on Sep. 14, 2020. 5 pages.
Wang et al., "Broadband achromatic optical metasurface devices." Nature communications 8.1 (2017): 1-9.
Wang et al., "Computational protein design with deep learning neural networks." Scientific reports 8.1 (2018): 1-9.
Wang et al., "Contact-free trans-pars-planar illumination enables snapshot fundus camera for nonmydriatic wide field photography." Scientific reports 8.1 (2018): 1-9.
Wang et al., "Room-temperature oxygen sensitization in highly textured, nanocrystalline PbTe films: A mechanistic study." Journal of Applied Physics 110.8 (2011): 083719. 9 pages.
Wang et al., "Structural, electrical, and optical properties of thermally evaporated nanocrystalline PbTe films." Journal of applied physics 104.5 (2008): 053707. 6 pages.
Witmer et al., "Comparison of ultra-widefield fluorescein angiography with the Heidelberg Spectralis® noncontact ultra-widefield module versus the Optos® Optomap®." Clinical ophthalmology (Auckland, NZ) 7 (2013): 389. 6 pages.
Wu et al., "RetCam imaging for retinopathy of prematurity screening." Journal of American Association for Pediatric Ophthalmology and Strabismus 10.2 (2006): 107-111.
Yu et al., "Light propagation with phase discontinuities: generalized laws of reflection and refraction." science 334.6054 (2011): 333-337.
Zhang et al., "Electrically Reconfigurable Nonvolatile Metasurface Using Optical Phase Change Materials." CLEO: Science and Innovations. Optical Society of America, 2019. 2 pages.
Zhang et al., "Ultra-thin high-efficiency mid-infrared transmissive Huygens meta-optics." Nature communications 9.1 (2018): 1-9.
Zhong et al., "Large-area metalens directly patterned on a 12-inch glass wafer using immersion lithography for mass production." Optical Fiber Communication Conference. Optical Society of America, 2020. 3 pages.
Zhou et al., "Multilayer noninteracting dielectric metasurfaces for multiwavelength metaoptics." Nano letters 18.12 (2018): 7529-7537.
Extended European Search Report in European App. No. 21780395.6 dated Feb. 27, 2024, 7 pages.
First Office Action with Search Report and translation in Chinese App. No.202180039349.4 dated May 30, 2026, 11 pages.

* cited by examiner

META-OPTICS-BASED SYSTEMS AND METHODS FOR OCULAR APPLICATIONS

CROSS-REFERENCE TO RELATED APPLICATIONS

This application is a continuation application of U.S. application Ser. No. 17/556,884, filed on Dec. 20, 2021 titled, "Meta-Optics-Based Systems and Methods for Ocular Applications," issued as U.S. Pat. No. 11,850,001, which is a continuation of U.S. application Ser. No. 17/164,425, filed on Feb. 1, 2021 titled, "Meta-Optics-Based Systems and Methods for Ocular Applications," issued as U.S. Pat. No. 11,206,978, which claims a priority benefit, under 35 U.S.C. § 119(e), of U.S. Application No. 63/003,782, filed on Apr. 1, 2020 titled, "Flat Optics-Based Systems and Methods for Ocular Applications", each of which application is incorporated herein by reference in its entirety.

GOVERNMENT SUPPORT

This invention was made with government support under HR0011-17-2-0029 awarded by the Defense Advanced Research Projects Agency. The government has certain rights in the invention.

BACKGROUND

Wide-angle optical imaging and projection systems are desirable for high-performance, wide field-of-view (FOV) imaging and projection applications. One of the earliest examples of a wide-angle optical system is the panoramic camera invented by Thomas Sutton in 1858. This panoramic camera included a single water-filled spherical lens that produced an image on a curved glass plate covered with reactive emulsion. Due to difficulties in fabrication and handling of curved plates, this approach was soon abandoned. Panoramic photography then evolved using planar detector planes while relying on compound lens assemblies, commonly known as fisheye lenses, to reduce optical aberrations at large viewing angles. Such a multi-lens architecture, however, increases the size, weight, assembly complexity, and cost of optical systems.

Fundus cameras have been widely used in retinal photography for the diagnosis and monitoring of retinal diseases. These cameras are used to image a large interior region of the eye and therefore benefit from wide FOV optics. For example, a fundus camera desirably should be capable of imaging a large region of the retina, sclera, or other tissues inside the eye. Imaging large regions in a single photo can require FOVs approaching 180 degrees.

Most conventional approaches to ocular imaging, like panoramic cameras, use complex lens systems to obtain wide FOVs. Fundus cameras are usually designed to illuminate and image the retina simultaneously using shared optical paths. Such optical systems are complicated and typically include a series of objective and condensing optical elements, beam splitters, mirrors, shadowing masks, diffusers, polarizers, light sources and photodetectors. State-of-the-art fundus cameras can be generally categorized into three groups: table-top fundus cameras, miniaturized hand-held ophthalmic cameras, and smart-phone-based ophthalmic cameras. Challenges associated with these existing technologies involve limited FOV, complicated illumination/imaging co-design, and poor signal-to-noise ratio. For example, cameras in each of the three groups have stacked or compound lenses and combine illumination and imaging optical paths. To date, high-quality, wide FOV retinal imaging is only offered by table-top fundus cameras built from complex and bulky optical systems. These cameras are large and expensive and must be operated at high-end and expensive clinical settings.

SUMMARY

Compact, wide field-of-view ocular imaging systems are described that are based on meta-lenses. The meta-lens can be a single flat-optic imaging element that can capture images over a FOV approaching 180 degrees or larger and focus the images onto an essentially flat or a curved focal plane. An ocular imaging system using a meta-lens may also use the pupil of the eye as an aperture stop for the imaging system to obtain high-resolution images. Such ocular imagers may be no thicker than 20 mm and have an input located a distance between 1 mm and 100 mm from an eye to obtain wide FOV, high-quality images of interior regions of the eye. In some cases, they can also be configured to be positioned in direct contact to the eye, or in contact via an intermediate layer, such as a contact lens or an immersion fluid layer positioned between the imager and the eye.

Such imaging systems can also be operated in reverse as a near-eye display systems. Instead of receiving images onto a detector array at the system's focal plane, the imaging systems can project wide-field images from the focal plane onto the retina or nearby screen for user viewing (e.g., for augmented reality (AR) or virtual reality (VR)). Variations of the near-eye display systems may also be used for eye-tracking applications. Because the imaging and near-eye display systems can have only a single focusing optic and no moving parts, the imagers and display systems can be compact, robust, and light-weight for easier deployment and use than conventional systems. The meta-lens based systems may have unprecedented size, weight, power and cost (SWaP-C) advantages compared to traditional bulk optical systems.

Some implementations relate to ocular imaging systems that comprise a substrate having a first surface with a meta-lens formed thereon. The meta-lens comprises an imaging zone having a first plurality of meta-atoms, wherein the meta-lens is to be positioned within 40 mm or within 100 mm of an eye's pupil to image an interior portion of the eye. The ocular imaging system may further include a light source to illuminate an interior of the eye and an array of photodetectors located at a focal surface of the meta-lens to detect an image of the interior portion of the eye that is formed by the imaging zone.

Some implementations relate to methods of operating an ocular imaging system. Such methods may comprise acts of: directing light from a light source toward an eye; collimating, focusing, or patterning the light with an illumination zone of a meta-lens, the illumination zone comprising a first plurality of meta-atoms formed on a substrate; focusing light reflected from the eye with an imaging zone of the meta-lens, the imaging zone comprising a second plurality of meta-atoms formed on the substrate; and detecting the focused light with an array of photodetectors.

Some implementations relate to near-eye display systems that comprise a substrate having a first surface with a meta-lens formed thereon. The meta-lens comprises a plurality of meta-atoms, wherein the meta-lens is to be positioned within 40 mm or within 100 mm of an eye's pupil. Such near-eye display systems may further include a micro-emitter array or micro-display located within 10 mm of the substrate to form an image that is projected by the meta-lens directly onto the retina of the eye, wherein the image covers a field-of-view between 70 degrees and 200 degrees as measured around the interior of the eye.

Some implementations relate to eye-tracking systems that comprise an emitter to produce illumination light and a first meta-lens that is within 10 mm of the emitter and within 40 mm or within 100 mm of an eye. The first meta-lens may include a first plurality of meta-atoms formed on a surface of a first substrate and arranged to project a pattern of the illumination light onto the eye. The eye-tracking systems may further include a second meta-lens located within 40 mm or within 100 mm of the eye's pupil. The second meta-lens may include a second plurality of meta-atoms arranged to image a region of the eye illuminated by the pattern and an imager having a plurality of photodetectors to record an image of the region of the eye.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally and/or structurally similar elements).

Figure 2A:
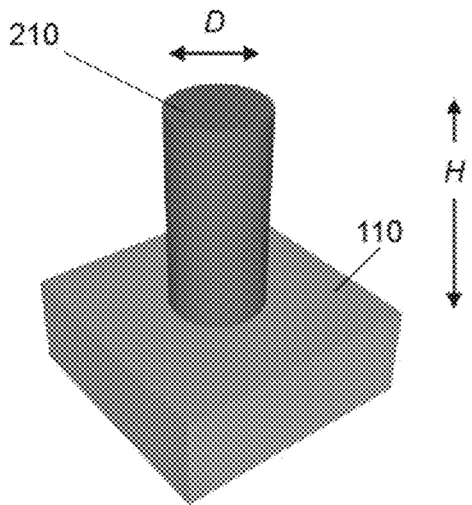
FIG. 2A shows a perspective view of a cylindrical pillar meta-atom for a WFOV meta-lens.
Figure 2B:
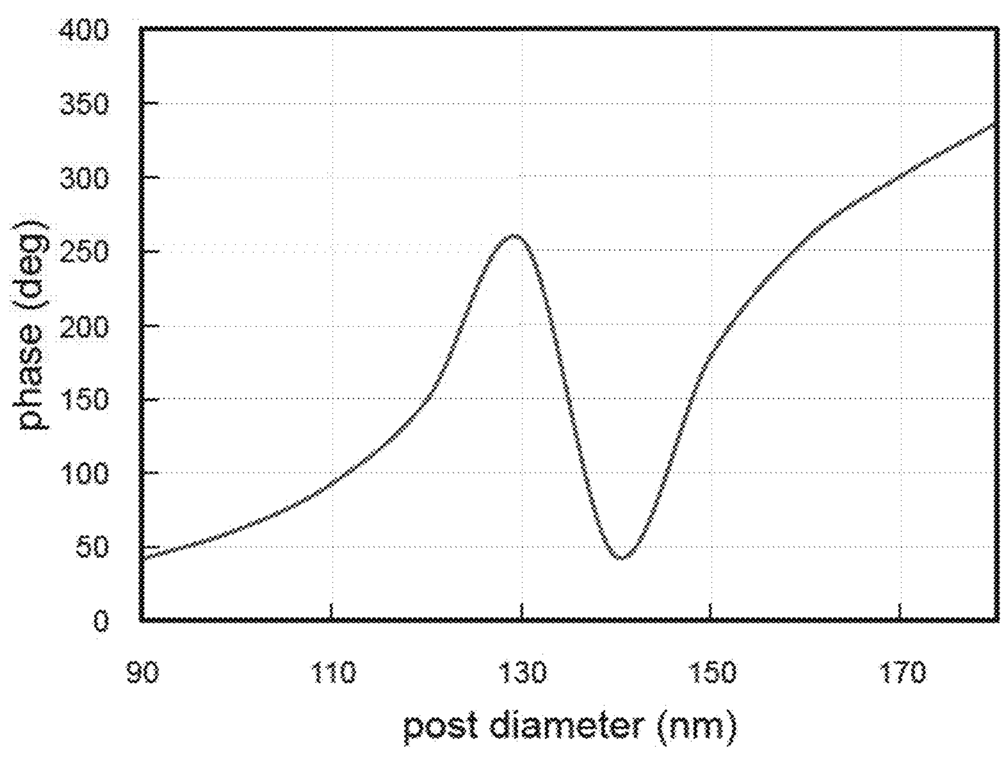

FIG. 2B plots transmittance and phase of cylindrical pillar meta-atoms for a WFOV meta-lens that are designed for an operating wavelength of 940 nm.

Figure 2C:
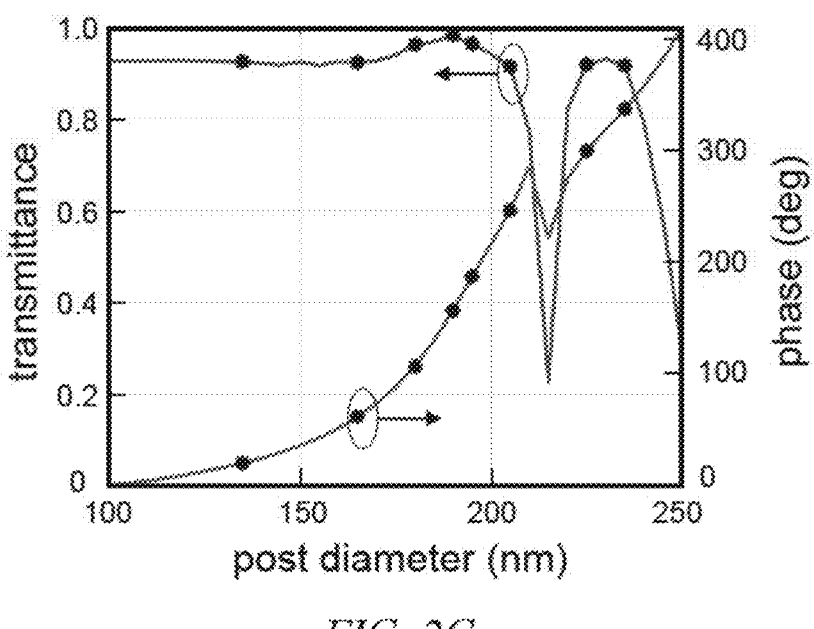

FIG. 2C plots phase of cylindrical pillar meta-atoms for a WFOV meta-lens that are designed for an operating wavelength of 680 nm.

Figure 3:
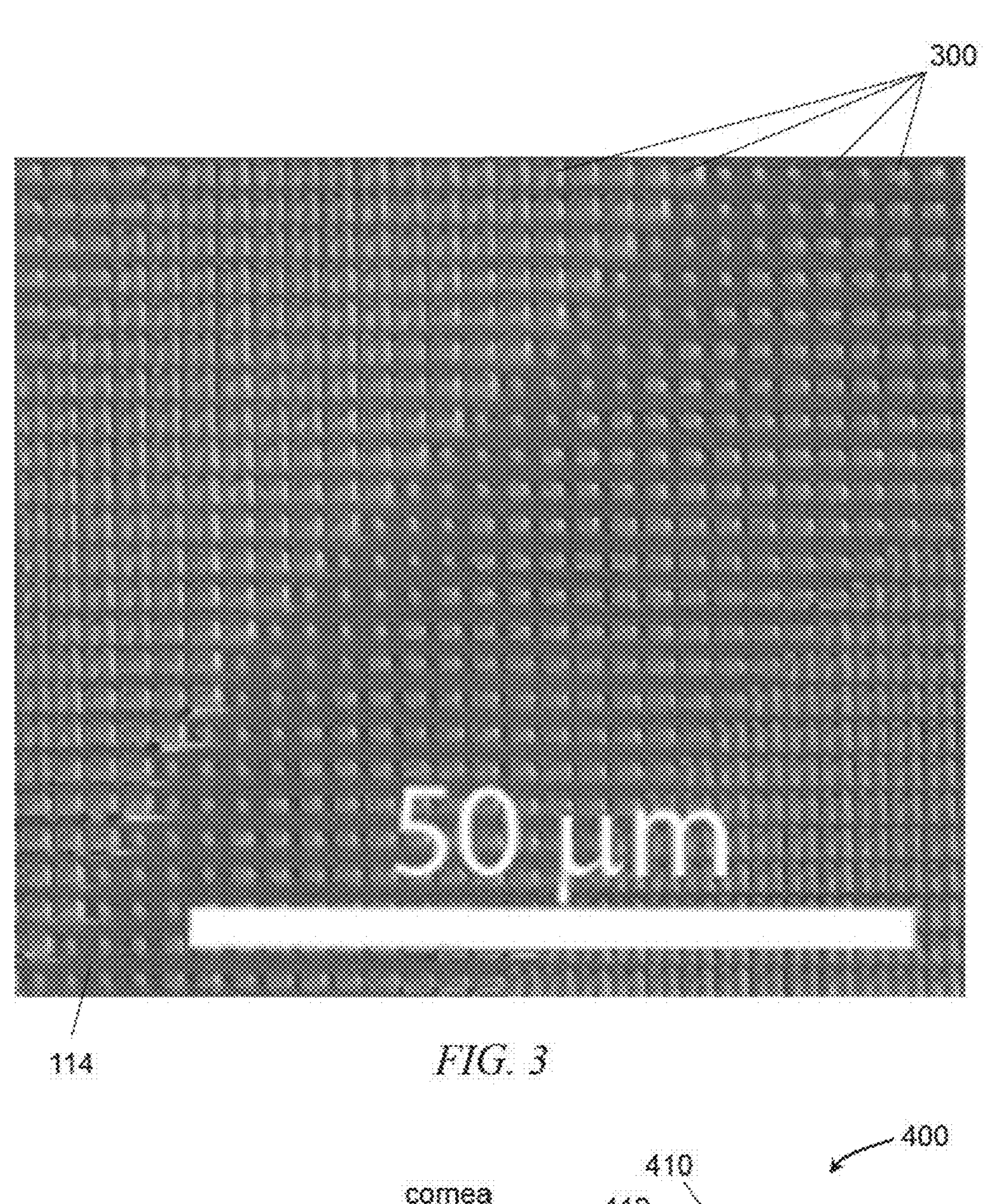

FIG. 3 is a scanning electron micrograph showing meta-atoms included in a portion of a meta-lens.

Figure 4:
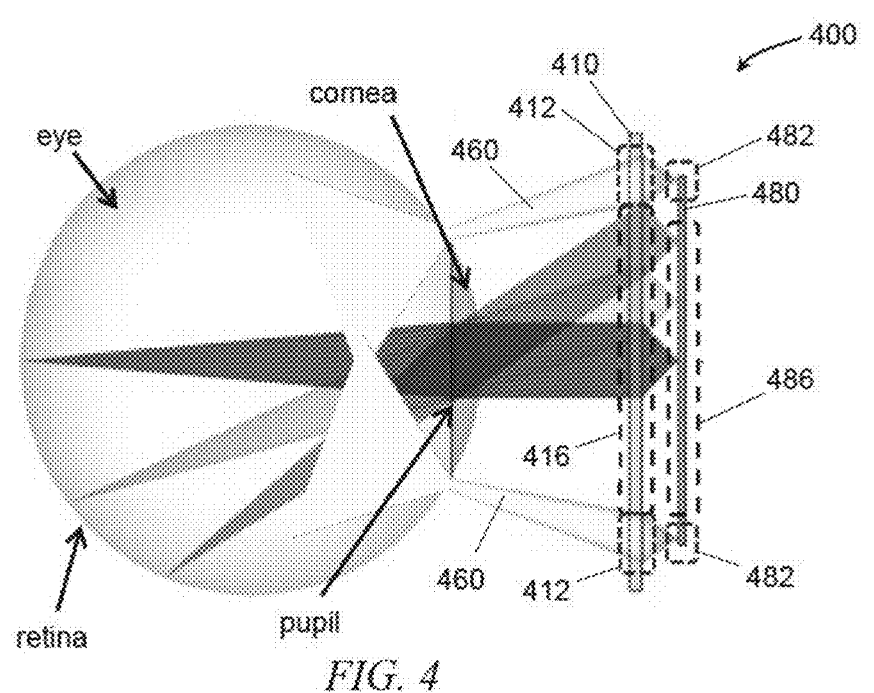

FIG. 4 depicts an example of an ocular imaging system that uses a compact meta-lens.

Figure 5A:
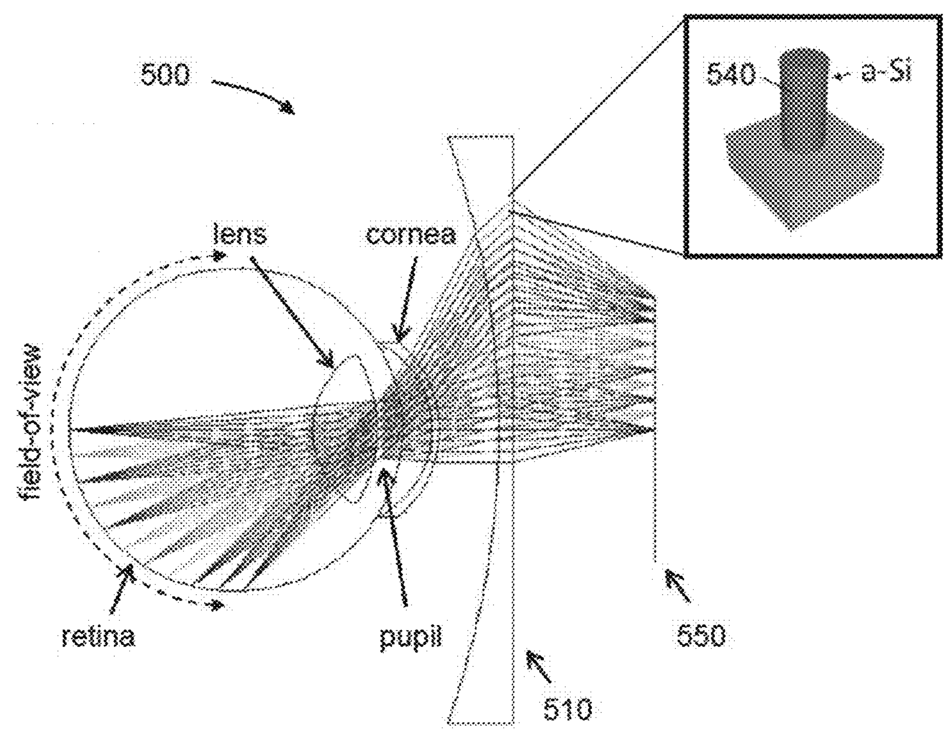

FIG. 5A depicts an example of a meta-lens for an ocular imaging system.

Figure 5B:
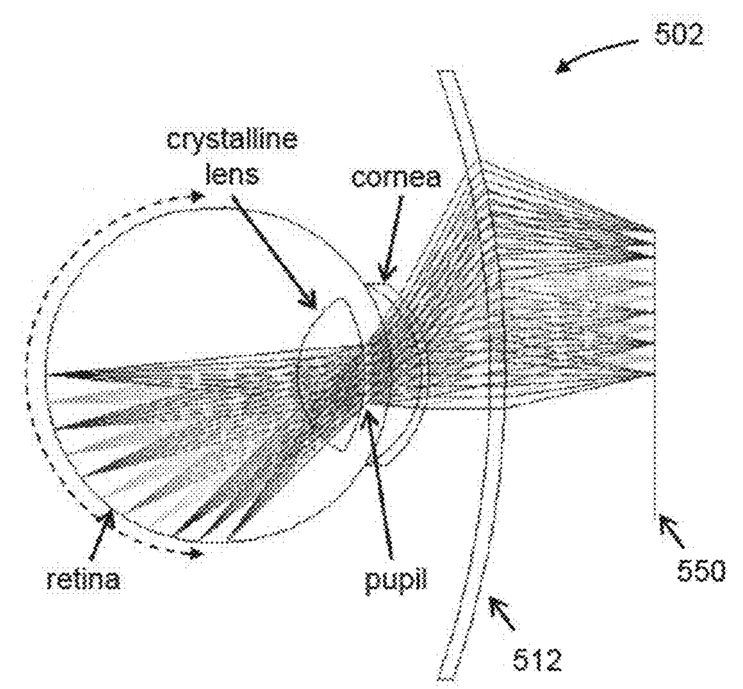

FIG. 5B depicts another example of a meta-lens for an ocular imaging system.

Figure 5C:
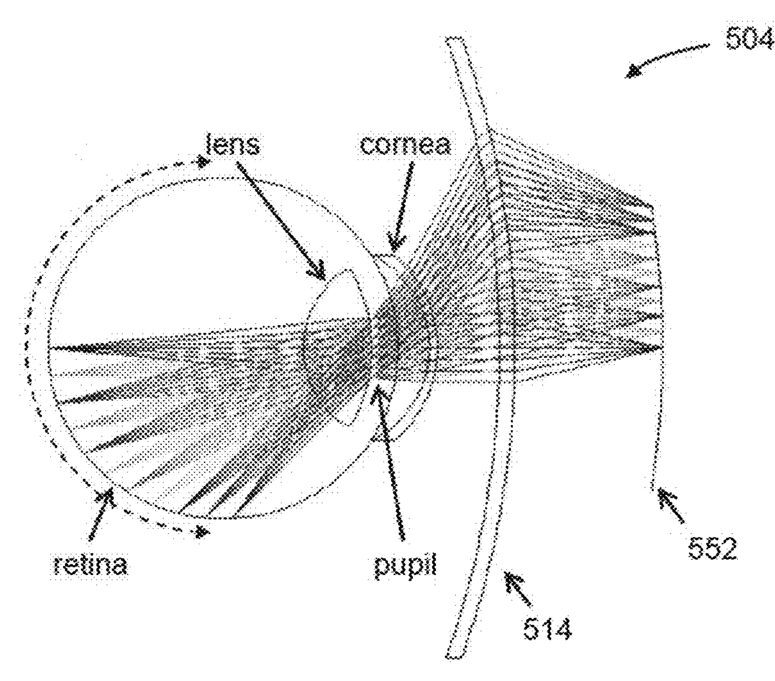

FIG. 5C depicts another example of a meta-lens for an ocular imaging system.

Figure 6:
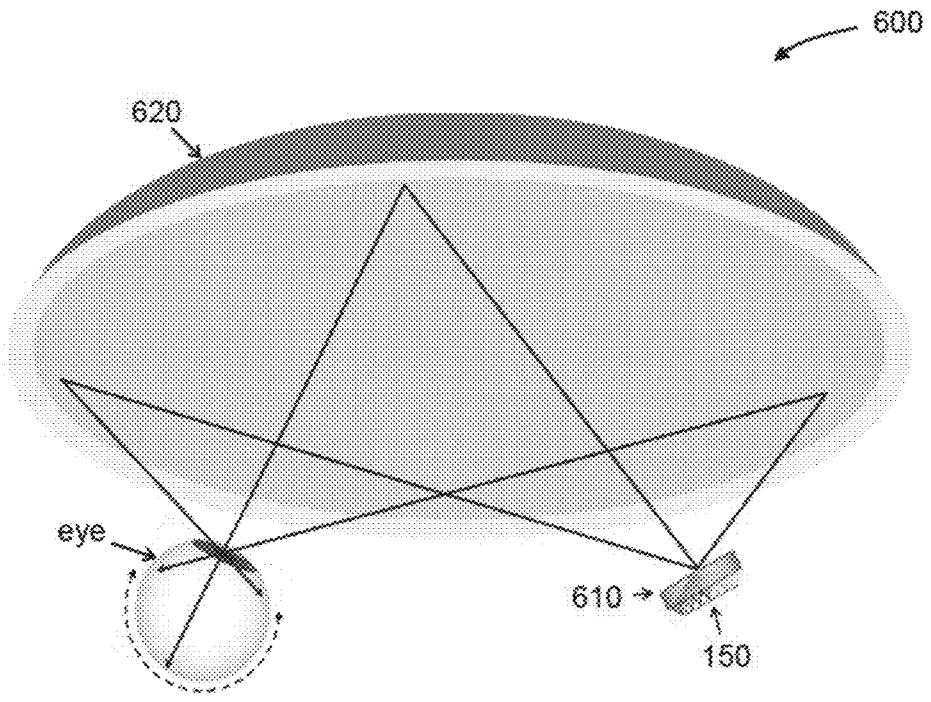

FIG. 6 depicts another example of an ocular imaging or near-eye display system that uses a compact meta-lens and a relay optic.

Figure 7:
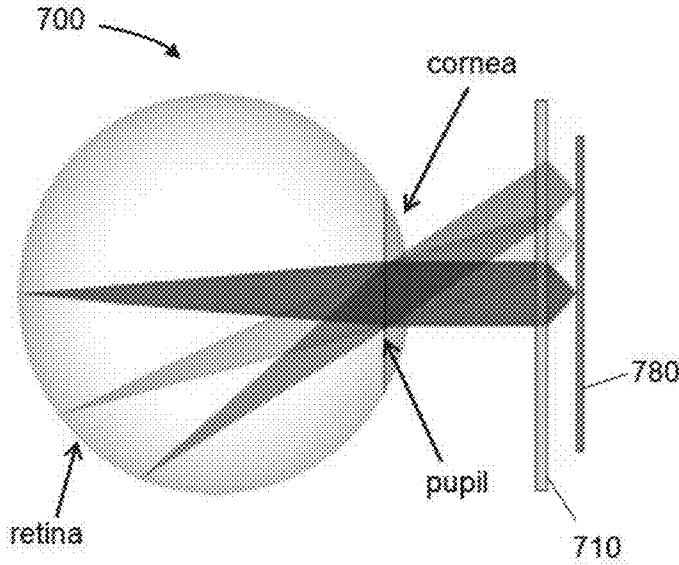

FIG. 7 depicts an example of a near-eye display system that uses a compact meta-lens.

Figure 8A:
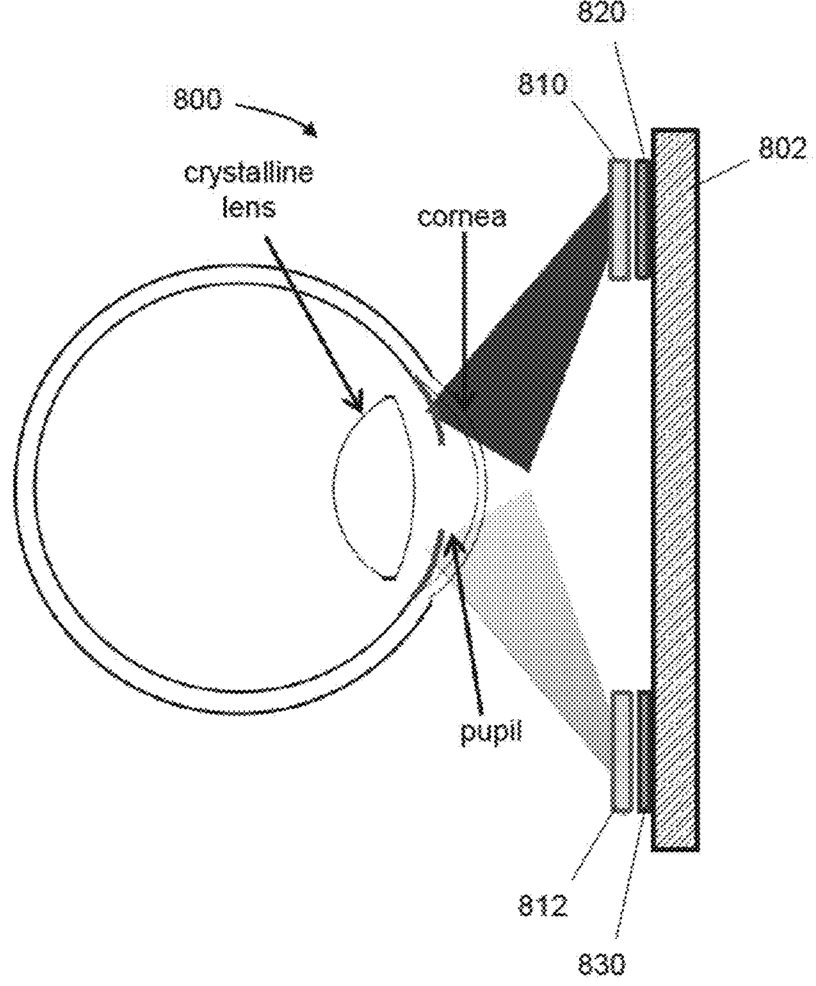

FIG. 8A depicts an example of an eye-tracking system that uses compact meta-lenses.

Figure 8B:
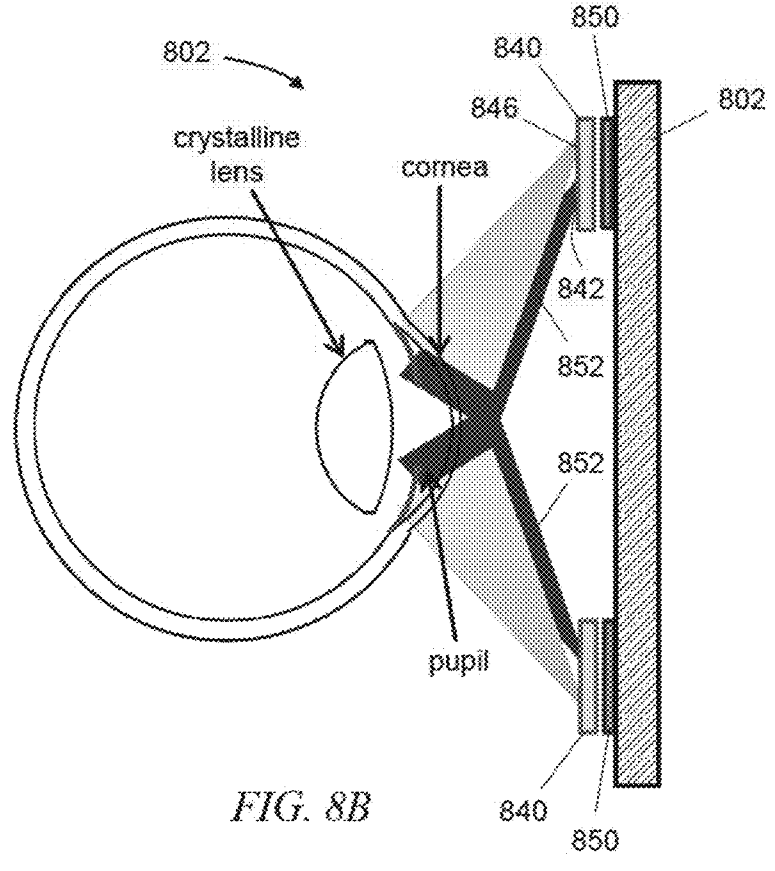

FIG. 8B depicts another example of an eye-tracking system that uses compact meta-lenses.

Figure 8C:
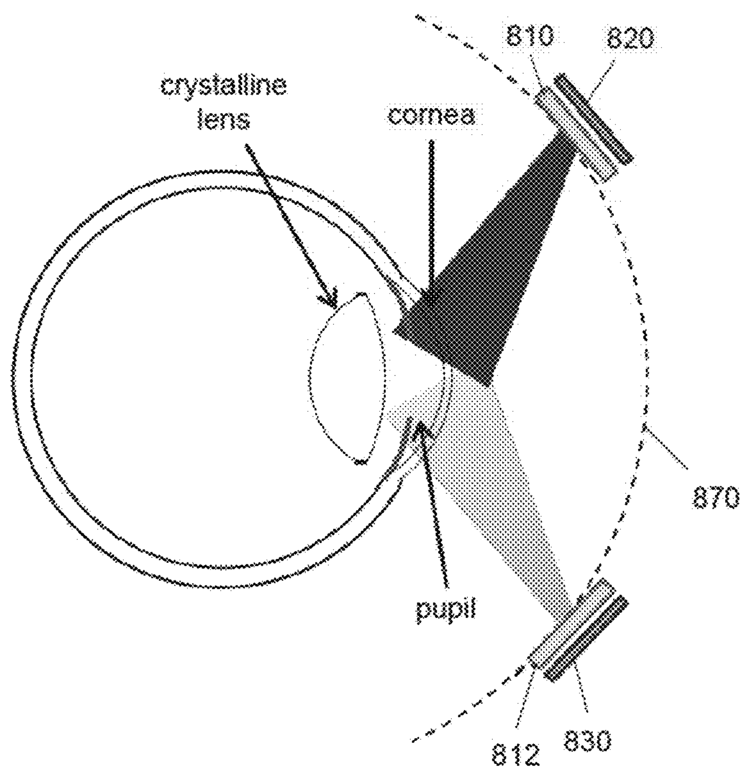

FIG. 8C depicts another example of an eye-tracking system that uses compact meta-lenses.

Figure 9:
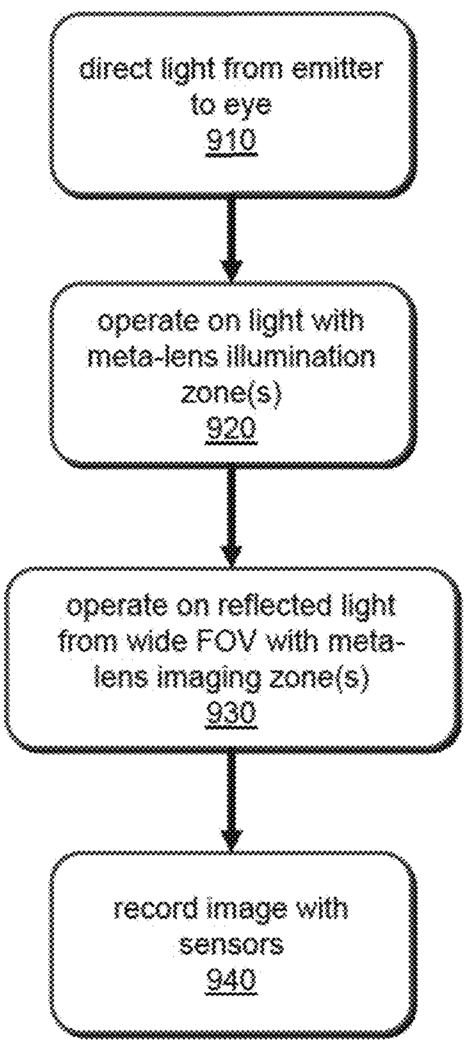

FIG. 9 illustrates acts that may be included in a method of operating an ocular imaging system.

DETAILED DESCRIPTION

Meta-lenses are compact optical elements that have microfabricated structures (called meta-atoms) formed on a transparent substrate. The meta-atoms are designed and located on the substrate to give the meta-lens its desired optical characteristics, which can be tailored for a particular application by an optical engineer. Because of their small size, lack of moving parts, robustness, and flexibly tailored optical characteristics, meta-lenses can be useful for various applications such as, but not limited to, augmented reality (AR), virtual reality (VR), heads-up display, near-eye display, three-dimensional (3D) sensing, holography, LIDAR, and Fourier transform optics. An optical system based on a meta-lens can have significant size, weight, performance, and cost (SWaP-C) advantages over a system made of traditional optical components. A meta-lens that is tailored for wide FOV imaging can be useful for ocular imaging and near-eye display, as described further below.

Figure 1:
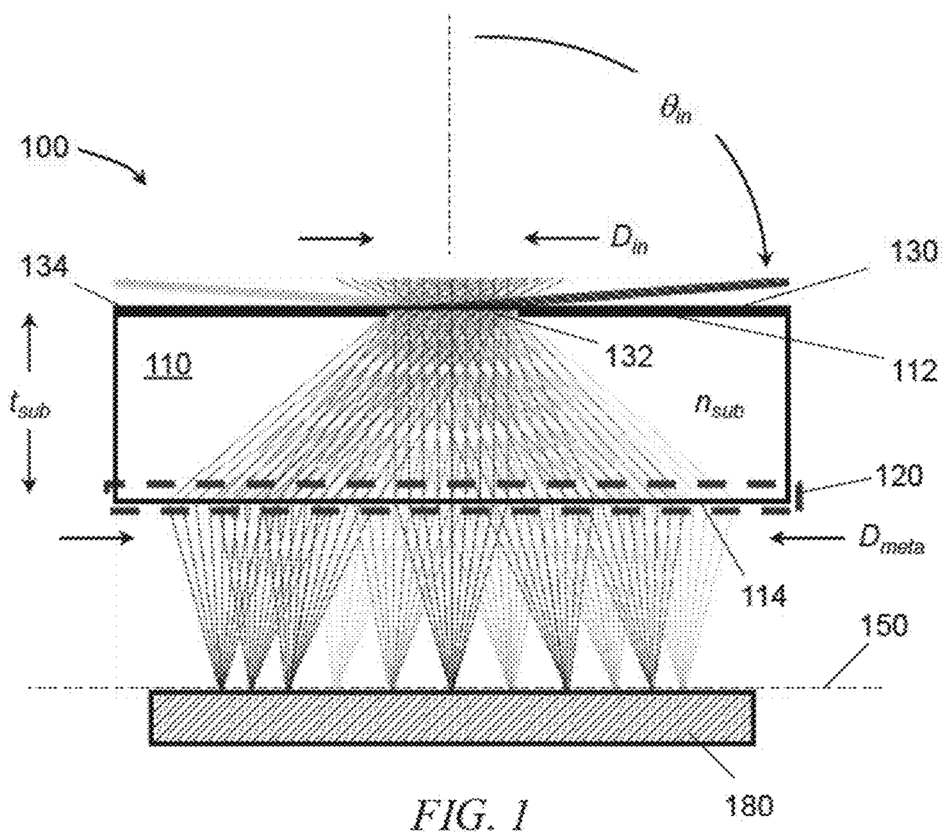
FIG. 1 depicts an elevation view of a wide field-of-view (WFOV) meta-lens.

FIG. 1 depicts an example of a meta-lens 100, which is monolithically integrated on a flat transparent substrate 110. The meta-lens includes an aperture stop 130 on a first surface 112 and a meta-surface 120 comprising meta-atoms formed on a second surface 114 of the substrate 110. For the illustrated example, the meta-atoms of the meta-surface 120 are arranged to focus collimated light received over a wide FOV onto a planar focal plane 150, as depicted in the drawing. An integrated circuit 180 (e.g., detector array, emitter array, and/or micro-display) can be placed at the focal plane 150 for image acquisition or image projection. Such a meta-lens can be used for wide-angle ocular imaging, near-eye display, and eye-tracking systems. Wide-angle ocular imaging, in particular, is desirable since it can address a wide range of diseases such as diabetic retinopathy, retinal vein occlusions, retinopathy of prematurity, retinal detachment, choroidal masses, uveitis, retinal vasculitis, etc.

The substrate 110 may be made of any suitable material that transmits light at the meta-lens's operating wavelength. The substrate 110 may be rigid, flexible, or stretchable and can be flat/planar on both sides, as shown in FIG. 1. In some cases, one or both surfaces of the substrate may be curved (e.g., concave or convex). For example, the substrate 110 may have a spherical, cylindrical, or free-form lens shape. In some cases, the substrate 110 may be warped, curved, or bent, depending on the application. Suitable substrate materials include but are not limited to calcium fluoride, halide crystals, sapphire, and other oxide crystals, quartz, silica, fused silica, chalcogenide crystals, glass (e.g., oxide, chalcogenide, as well as other types of glass), optical polymers, or semiconductor materials. The substrate material can be transparent and exhibit low loss (e.g., less than 10%) at the operating wavelength of the meta-lens. The substrate 110 has a refractive index of $n_{sub}$ and a thickness of $t_{sub}$. Light beams entering the input aperture 132, which has a diameter of $D_{in}$, at different incidence angles $\theta_{in}$ are refracted to the backside meta-surface 120, which has a total diameter of $D_{meta}$. The light beams are then focused by the meta-surface's meta-atoms onto the planar focal plane 150.

The aperture stop 130 can be formed as a layer 134 of opaque material (e.g., absorptive or reflective metal or semiconductor material) on the first surface 112 of the substrate 110. In one example, the aperture 132 can be circular with a diameter given by:

$$D_{in} = D_{meta} - 2t_{sub}\tan\left[\sin^{-1}(1/n_{sub})\right] \quad (1)$$

This diameter can range from microns to millimeters, with a numerical aperture (NA) that ranges from 0 to 1. The numerical aperture can be higher (e.g., 1.5) if the meta-lens is immersed in oil or other high-index material.

The aperture 132 can be square, elliptical, hexagonal, rectangular, or any other suitable shape in other implementations. Alternatively, the aperture can include one or more sub-apertures, sub-regions, patches, or arrays configured to modulate or encode the input light in one or more of spectrum, phase, amplitude, polarization, etc. For example, at least a portion of the aperture 132 may be patterned with meta-atoms that filter light passing through the aperture 132. If desired, the edge of the aperture stop 130 can be apodized, e.g., with a Gaussian or super-Gaussian apodization, to reduce deleterious edge effects that might arise from an abrupt edge of the aperture.

In some ocular imaging implementations, the aperture stop 130 and aperture 132 may not be included on the substrate 110. Instead, the pupil of a subject's eye or an aperture positioned near the eye (e.g., an artificial aperture on a contact lens) may be used as the aperture stop for an ocular imaging or near-eye projection optical system. In such cases, the meta-lens 100 may be specified for use in close proximity to the eye (e.g., within 100 mm, within 40 mm, within 20 mm, within 10 mm, or within 5 mm from a surface of the eye). The specified distance may be between a designated location on the meta-lens (e.g., its rear meta-surface 120) or a location on the assembly in which it is mounted (e.g., a mark on the assembly) and a designated feature of the eye (e.g., cornea, exterior surface, or pupil). In some cases, the working distance of a meta-lens may be between 4 mm and 11 mm to maintain a FOV greater than 60 degrees.

In some implementations, the ocular imaging system may include range-finding apparatus to aid a user in positioning the meta-lens 100 a correct distance from the eye. For example, the integrated circuit 180 may include one or more laser diodes and the meta-lens include an illumination zone described further below that projects a pattern onto the eye, which can be imaged back on the focal plane 150 and integrated circuit 180 by the meta-lens. The image of the pattern can be processed to determine a distance between the meta-surface 120 and pupil, for example.

The meta-surface 120 includes a plurality of meta-atoms (sometimes referred to as Huygens meta-atoms, nano-antennae, or nano-structures) that modify the amplitude, phase, and/or polarization of incoming wave fronts. These meta-atoms can have sub-wavelength feature sizes (in vertical and/or transverse dimensions), wherein the reference wavelength is the designed operating wavelength for the meta-lens. The meta-atoms may be 0.01 wavelength to 100 wavelengths thick. There can be one or more types of meta-atoms formed on the substrate's meta-surface 120. For example, the meta-atoms may have one or more of the following shapes: square, rectangular, bar, beam, cylindrical or elliptical (pillars or discs), rings, crosses (+), X-shaped (x), V-shaped, H-shaped, L-shaped, or freeform shapes. The shapes are not so limited, and other shapes may be used.

The types of meta-atoms may be categorized into three groups: resonating structures, vertical waveguiding structures, and geometric phase-based structures. There may be more than one size and shape of meta-atoms in each of these three groups. In some cases, a same meta-atom shape may be used in two or more of the groups. The resonating structures include Huygens meta-atoms and may have one or more dimensions that is an integral number of half-wavelengths of the designed operating wavelength, divided by the refractive index of the material from which the meta-atom is made. Accordingly, the operating wave may resonate in these structures. The vertical waveguiding structures may form a vertical waveguide for the operating wavelength. The phase-based structures may be designed to impart a desired phase shift to TE and/or TM waves passing through each unit cell containing a meta-atom or passing through a portion of the meta-surface 120 containing adjacent identical unit cells. A meta-surface may be formed using one type of meta-atom or a combination of two or three types of meta-atoms.

The meta-atoms can be arrayed on a lattice with a pitch that is less than or equal to the operating wavelength of the meta-lens 100. The lattice can have any suitable structure (e.g., square, rectangular, or hexagonal). The lattice can be periodic, semi-periodic, aperiodic, or randomly spaced for example, with lattice spacing defined by a center-to-center distance between adjacent meta-atoms. The meta-atoms' shapes, sizes, and layout can be selected so that the meta-surface's spectral response does not change with angle of incidence. The meta-atoms can be shaped and located to provide a desired phase profile over the entire meta-surface 120. In some cases, the first surface 112 may additionally have meta-atoms patterned thereon to further control optical characteristics of the meta-lens 100. Further details of meta-lens design, fabrication, and operation can be found in U.S. patent application Ser. No. 16/894,945 titled "Ultra-Wide Field-of-View Flat Optics," filed Jun. 8, 2020, which application is incorporated herein by reference in its entirety.

FIG. 2A shows a perspective view of a cylindrical pillar meta-atom 210. Depending on its size and material used, a cylindrical pillar meta-atom may be used as a resonating meta-atom, vertical waveguiding meta-atom, or geometric phase-based meta-atom. The meta-atom 210 has a height H extending from the surface of the substrate 110 and a diameter D. For the illustrated example and graphs of FIG. 2B and FIG. 2C, the meta-atom 210 is formed from amorphous silicon and the substrate 110 is formed from sapphire. The meta-atom 210 is located in a square-shaped unit cell, and there can be thousands to millions of such unit cells distributed side-by-side across the surface of the substrate 110 in a square lattice. The diameters D and/or heights H of the meta-atoms 210 can be varied among the unit cells across the surface to obtain the desired spatial phase characteristics across the surface of the substrate 110.

As one example, a metal-lens for ocular imaging at an operating wavelength of 680 nm may have a meta-surface 120 with cylindrical pillar meta-atoms 210 of eight different diameters that are distributed across the meta-surface 120. The heights H of the meta-atoms may be the same (e.g., 800 nm). The unit cell may be square and measure 320 nm on each side. The eight diameters of the meta-atoms 210 are listed in Table 1.

TABLE 1

Diameters of example cylindrical pillar meta-atoms for a meta-lens.

| | Meta-atom number | | | | | | | |
|---|---|---|---|---|---|---|---|---|
| | 1 | 2 | 3 | 4 | 5 | 6 | 7 | 8 |
| D (nm) | 90 | 100 | 112 | 120 | 150 | 156 | 166 | 185 |

FIG. 2B plots phase characteristics of unit cells of a meta-surface 120 having cylindrical pillar meta-atoms 210. The meta-atoms may have diameters as listed in Table 1. The eight meta-atoms with various phase delays can cover a phase range of approximately 360 degrees with steps of about 45 degrees.

FIG. 2C shows transmittance and phase characteristics for different meta-atoms that can be used for a longer-wavelength application. The transmittance and phase are plotted as a function of pillar diameter D for unit cells containing cylindrical pillar meta-atoms 210. The pillars are formed from amorphous silicon and the substrate 110 is sapphire. These meta-atoms are designed for a meta-lens having an operating wavelength of 940 nm. Eight pillar diameters ranging from about 130 nm to about 230 nm can provide various phase delays over a range of about 360 degrees with steps of about 45 degrees and transmittance above 90%.

Materials other than silicon may be used for the meta-atoms. For example, various dielectric, semiconductor, or metal materials may be used for the meta-atoms that are amenable to micro-fabrication processes. Example semiconductor materials include, but are not limited to, silicon-carbide, indium-phosphide, gallium-nitride, gallium-arsenide, etc. Other meta-atom materials include silicon nitride ($SiN_x$) and titanium dioxide ($TiO_2$). Lead telluride (PbTe) can be used as a meta-atom material with a calcium fluoride ($CaF_2$) substrate for mid-infrared wavelengths. The meta-atoms can also be directly etched into a substrate, e.g., a silicon substrate.

In some cases there may be no more than 10 different shapes of meta-atoms on a lens' meta-surface 120. However, fewer or more shapes may be used for some implementations. In some cases, there may be at least two different shapes of meta-atoms on a lens' meta-surface 120. In some cases, there may be up to 100 or more different shapes of meta-atoms on a lens' meta-surface 120.

FIG. 3 depicts a portion of a meta-lens' meta-surface 120 designed for a mid-IR imaging application. An array of meta-atoms 300 are patterned across the surface 114 of the substrate. The meta-atoms include rectangular and H-shaped structures arranged on a square lattice (2.5-micron pitch). In some implementations, similar shapes and/or sizes of meta-atoms may be located within radial bands on the substrate. For example, there may be a plurality of cylindrical pillar meta-atoms having a same diameter located within a radial band on a meta-surface. There may be a plurality of different radial bands containing different shapes formed on the substrate. The different radial bands may extend across portions of the meta-surface 150 to define desired phase characteristics of the meta-surface.

By spatially decoupling the meta-surface 120 and aperture stop 130, the meta-lens 100 can capture input beams at different angles of incidence (AOIs) on different yet continuous portions of the meta-surface 120. This can allow local tailoring of the lens' phase profiles, e.g., by optimizing against a figure of merit that accounts for focusing quality at multiple AOIs. The meta-surface phase profile can be designed so that the root-mean-square (RMS) wave front error from an ideal spherical wave front over the input aperture is always smaller than 0.0745 wavelengths. With such low wavefront errors, the meta-lens 100 can have a Strehl ratio of over 80% (and achieve near diffraction-limited performance) over a very wide field-of-view, which can be 120°, 130°, 140°, 150°, 160°, 170°, 175°, 179°, or nearly 180° for a flat substrate 110. For meta-lens with a curved, bent, or warped substrate, the field-of-view can be 180° or larger. Such large FOVs can be beneficial for ocular imagers and near-eye display systems.

Such meta-lenses can have meta-surfaces that correct one or more third-order Seidel aberrations, including coma, astigmatism, and field curvature. An example meta-lens 100 for an ocular imager or near-eye display system can have an aperture 132 with a diameter between 5 microns and 5 centimeters. There may be hundreds of thousands or millions of meta-atoms patterned on the meta-surface 120 of the meta-lens 100, and a diameter of the area over which the meta-atoms are patterned may be between 100 um and 50 mm. A thickness of the meta-lens may be between 50 microns for membranes and 50 mm, and a focal length of the meta-surface can be between 0.1 mm and 50 mm.

FIG. 4 depicts an example of an ocular imaging system 400 that uses a compact meta-lens 410. The ocular imaging system 400 can include the meta-lens 410 spaced apart from an integrated circuit 480 and an aperture stop (which is the pupil of the eye in the illustrated example). The meta-surface of the meta-lens 410 and integrated circuit 480 may be separated by a distance having a value between 0.1 mm and 50 mm and may be mounted together within a common case. The case may include adjustment mechanisms, such as screws and/or piezoelectric positioners, to adjust one or more of parallelism, distance, lateral position, and rotation between the meta-lens 410 and the integrated circuit 480. The meta-lens can be designed as a wide FOV lens, e.g., a FOV between 70° and 200° as described above, to form an image of a large portion of the retina onto the flat integrated circuit 480. The ocular imaging system 400 may be specified for use (or designed for use) within a certain distance from the eye (for example, a distance of 2 mm and 100 mm between the meta-surface of the lens and the pupil of the subject's eye being examined), so that the eye's pupil functions as an aperture stop for the imaging system. When located closer to the eye, the diameter of the meta-lens can be reduced compared to a meta-lens located farther from the eye. For example, when located close to the eye, the area on the meta-surface 120 that includes meta-atoms for wide FOV imaging may have a diameter between 5 mm and 15 mm.

In some implementations, the case supporting the meta-lens 410 and integrated circuit 480 may be formed to contact the subject's forehead and/or cheek bone to hold the meta-lens at a suitable distance from the subject's eye and pupil. Because the ocular imaging system 400 may include only a meta-lens 410 and integrated circuit 480, the case supporting these elements may be no more than 20 mm thick and may measure no more than 60 mm on a side in some cases, or no more than 100 mm on a side in some implementations. A volume of the ocular imaging system 400 may be no greater than 60 $cm^3$ in some cases, or no more than 100 $cm^3$ in some implementations.

The integrated circuit 480 can include an imaging region 486 and one or more illumination regions 482, which may be formed on a same substrate and/or located on a same plane. The imaging region 486 may contain an array of photodetectors (e.g., a CCD or CMOS imaging array) along with read-out circuitry. For low light levels, the photodetectors may comprise avalanche photodiodes. The photodetectors and read-out circuitry are used to acquire electronic images of the retina or other tissues formed by the meta-lens 410. The integrated circuit 480 may connect to a computer or smart phone, so that the electronic images may be stored and/or processed. An illumination region 482 can include one or more light-emitting devices (e.g., light-emitting diode(s), vertical-cavity surface-emitting laser(s), laser diode(s), etc.) that produce an illumination beam 460. In some implementations, the illumination region 482 can be annular and surround the imaging region 486. The illumination beam(s) 460 may be directed at the eye and may or may not enter the eye through its pupil. For example, the illumination beam(s) may enter the eye through the ciliary muscle or sclera and scatter from such tissue to illuminate a large portion of the interior eye and tissues of interest therein. By introducing light into the eye off-axis and away from the pupil, back reflections from interfaces through the pupil that contribute to imaging noise and/or background signal can be reduced.

The meta-lens 410 may include an imaging zone 416 that corresponds to the imaging region 486 and one or more illumination zones 412 that correspond to the illumination region(s) 482 of the integrated circuit 480. The imaging zone 416 and illumination zone(s) 412 can include a plurality of meta-atoms formed on the meta-surface of the meta-lens 410. In some cases, the meta-atoms are formed on a back surface of the meta-lens that is away from the eye. In other cases, the meta-atoms may be formed on a front surface of the meta-lens that is closest to the eye. In yet other cases, meta-atoms may be formed on the front and back surfaces of the meta-lens 410.

Meta-atoms formed in the imaging zone 416 can be as described above to image a wide FOV of the retina onto the flat imaging region 486 of the integrated circuit 480. In addition to correcting for Seidel aberrations, these meta-atoms may also account for changes in object distances to different portions of the retina. Meta-atoms formed in the illumination zone(s) 412 can be arranged to collimate or focus light from emitters in the illumination region 482 onto the eye. Accordingly, the pattern and functionality of meta-atoms in the illumination zone(s) 412 can differ from the pattern and functionality of meta-atoms in the imaging zone 416.

In operation, light emitted from emitters in the illumination region(s) 482 is coupled by the illumination zone(s) 412 to illuminate the retina or other tissues of interest in the eye. Light reflected by the retina or other tissues is coupled by the imaging zone 416 onto the imaging region 486 to generate images of the retina or other tissues over a wide FOV. In one example, the illumination beams 460 from the illumination region(s) 482 are coupled by at least one illumination zone 412 of the meta-lens 410 to illuminate the pupil, palpebral, scleral, and/or pars-planar with a prescribed pattern (e.g., a ring pattern) to either directly or diffusely illuminate the retina. This illumination may yield a large, uniformly-illuminated retinal region and exhibit reduced back reflections from the cornea into the imaging optical path. The eye's pupil acts as an aperture stop for the meta-lens and optical system to achieve high-resolution images over the wide FOV.

Although the emitters, photodetectors, illumination zone(s) 412 and imaging zone 416 are segregated on their respective substrates in the illustrated example of FIG. 4, they may not be segregated in other implementations. For example, the illumination zone(s) 412 and imaging zone 416 can be overlapped to achieve multiplexed functions in a same area of the meta-lens 410. This is possible because of the flexible design offered by shaping and arranging the meta-atoms on the lens' meta-surface. In an overlapped configuration, the emitters may be located (e.g., interspersed) within a same area of the integrated circuit 480 as photodetectors.

Additionally, optical filtering is possible with the meta-atoms on the lens' meta-surface. An optical filter may be used to allow a desired range of wavelengths to be passed or rejected. The meta-atoms can be designed to provide such additional functionalities. For example, silicon nano-posts can be designed to block light with wavelengths shorter than approximately 650 nm while passing longer wavelengths for imaging.

The ocular imaging system 400 of FIG. 4 can exhibit several improvements over conventional ocular imaging systems. The ocular imaging system 400 can exhibit an improved single-shot FOV having a value between 70° and 200°. Larger FOVs may be possible with curved substrates or other optical arrangements as described further below. These FOV values are expressed in terms of eye angle (i.e., measured as a spherical angle around the interior of the eye) rather than external incidence angle. Such large FOVs are a significant improvement over conventional fundus cameras that typically achieve a single-shot FOV up to about 60°. Conventional fundus cameras are limited by the acceptance angle of bulky optical lens systems that correct angle-induced aberrations and an unavoidable distance between the eye's pupil and entrance aperture of the bulky lens system. Although some conventional fundus cameras with moving components (scanning mirrors) can achieve very high FOVs, these cameras are mechanically complicated, expensive, and require a skilled operator in a clinical setting.

The ocular imaging system 400 can exhibit improved illumination and imaging co-assemblies. For example and as seen in FIG. 4, a same substrate for the meta-lens 410 can be used for forming images of the interior eye and for shaping and guiding illumination light into the eye. Additionally, the photodetectors for imaging and emitters for illumination may be mounted on a same plane and/or substrate or on parallel planes. In contrast, illumination and imaging paths of conventional fundus cameras usually involve complex and bulky optical system that form a common optical path for illuminating and imaging the retina. Some traditional fundus cameras illuminate directly through the pupil (i.e., trans-pupillary illumination) by generating a ring-shaped pattern around the peripheral region of the pupil to minimize back reflection. Such designs are typically complex with limited FOV and poor illumination uniformity. Additionally, pupillary dilation is often required. Trans-scleral, trans-palpebral, and trans-pars-planar illumination methods have been proposed for wide-FOV fundus imaging without the need for pupil dilation. However, in such conventional approaches external light sources (e.g., LEDs or fiber-coupled sources) are brought in close proximity to the eye to illuminate the retina. Such separately-assembled illumination units, sometimes in direct contact with the eye lid, demand precise alignment and pose challenges for device miniaturization.

The ocular imaging system 400 can further exhibit improved signal-to-noise ratios over conventional systems. Off-axis illumination of the retina by introducing light through regions of the eye other than the pupil (as depicted in FIG. 4) can reduce glare (noise) that would otherwise arise from reflections from multiple optical surfaces if the illumination light were introduced along an imaging path through the pupil (as done for most conventional fundus cameras). Such a reduction in glare is beneficial for improving signal-to-noise since the desired signal is a weak reflection of illumination light from the retina or other tissues of interest.

Another advantage of the ocular imaging system 400 is that the system's meta-lens can be readily designed for operation at a single wavelength, multiple wavelengths, or a broad range of wavelengths. One or more light-emitting devices can be included in the integrated circuit 480 to emit light at the desired operating wavelength(s). Once the operating wavelength(s) is or are known, numerical computation is performed to design the shape and arrangement of meta-atoms on the lens' meta-surface to achieve desired imaging and illumination functionality. Operating wavelengths may include visible to IR wavelengths. For example, visible wavelengths can be used for near-eye display. One or more of visible, near IR, and longer wavelength IR may be used for ocular imaging.

Because of their small size and low part count, in some cases the meta-lens 410 and/or integrated circuit 480 may be swappable during use. As one example, there may be a plurality of meta-lenses 410 and/or integrated circuits 480 on a wheel that are designed to operate at different wavelengths. A first selected pair or an integrated circuit 480 may be rotated into position to obtain first ocular images at a first wavelength or range of wavelengths. The first wavelength(s) may be designed to preferentially image blood vessels, for example. A second pair or an integrated circuit 480 may then be rotated into position to obtain second ocular images at a second wavelength or range of wavelengths. The second wavelength(s) may be designed to preferentially image retinal tissue, for example. In some cases, rotatable components may not be necessary. Instead, a single meta-lens 410 may be designed to provide sufficient imaging for all wavelengths of interest and different emitters may be included on the same integrated circuit 480. In such a case, the different emitters may be cycled on and off in sequence to illuminate the eye with a sequence of different wavelengths.

Other meta-lens structures and ocular imaging systems are also possible. FIG. 5A, FIG. 5B, and FIG. 5C depict ray-tracing results for several ocular imaging systems 500, 502, 504 having different meta-lens designs. For each of the designs, the meta-lens comprises a sapphire substrate. The meta-atoms are formed from silicon and all are shaped as cylindrical nano-pillars 540 of various diameters, of which an example is depicted in the inset of FIG. 5A. There is a sub-wavelength spacing between the pillars. In these designs, the pupil of the eye is used as the aperture stop of the ocular imaging system to achieve high-resolution images over a wide FOV. The ray-tracing model assumes a pupil diameter of 4 mm and a 4 mm separation distance between the cornea and the front surface of the meta-lens. In some cases with different meta-lens design, the separation distance may be between 2 mm and 100 mm. Meta-atoms 540 are patterned on a back surface of the meta-lens and image the retina onto a focal surface 550, 552 over a wide FOV with significantly reduced aberrations. The meta-lens is designed to have an effective f-number of between 0.5 and 10, though other values can be readily achieved with different design of the meta-lens. The total thickness of the ocular imaging system (excluding the pupil) can be between 5 mm and 50 mm with a single focusing optical element.

In FIG. 5A, the meta-lens 510 has a planar back surface on which silicon nano-pillars 540 are patterned. These meta-atoms focus incoming rays onto a flat focal plane 550, where an integrated circuit may be located. The front surface of the meta-lens 510 can be curved (e.g., spherically concave) as shown. With a different arrangement of meta-atoms, the front surface of the meta-lens 510 may be flat as depicted in FIG. 4. The FOV for the illustrated meta-lens is over 180°, as measured around the interior of the eye.

FIG. 5B illustrates another implementation where the meta-lens 512 comprises a curved substrate. The meta-atoms may be formed on the back surface of the substrate when the substrate is flat, and the substrate may be subsequently deformed (e.g., suctioned under vacuum or heated and deformed into a spherically-shaped shell). The meta-atoms are arranged to focus the rays onto a flat focal plane 550. The FOV for the illustrated meta-lens is over 180°.

FIG. 5C illustrates another implementation where the meta-lens 514 comprises a curved substrate. The meta-atoms may be formed on the back surface of the substrate and are arranged to focus the rays onto a curved focal surface 552. The eye-angle FOV for the illustrated meta-lens is over 180°. For such an implementation, the integrated circuit may be formed on a flat and flexible substrate that is subsequently deformed into a spherical shape.

By including at least one curved surface on a meta-lens and/or focusing to a curved focal plane as depicted in FIG. 5A through FIG. 5C, the FOV may be increased significantly (e.g., by at least 30°) over the FOV for the implementation shown in FIG. 4. Potentially, the entire retina may be imaged in a single shot with such ocular imaging systems, which is not possible with conventional ocular imaging systems. Introducing curved surfaces may facilitate other 3D imaging, sensing, or illumination functions. The ability to flexibly design wavefront shaping with the meta-lens allows geometric modifications of the meta-lens substrate and/or focal plane, which can be decoupled from the system's optical functionality. Such geometric modifications may significantly improve light capturing at large angles, facilitate system integration, and allow ergonomic designs tailored for human body shapes for applications such as ocular imagers, wearable medical devices, head mounted displays, etc. In some cases, a conformal optical meta-lens-based system can be placed in contact with the eye, for example, by integration into a contact lens. In addition, both substrate surfaces of a meta-lens can be patterned with meta-atoms to further enhance wavefront control.

FIG. 6 depicts another implementation of an ocular imaging system 600 or near-eye display system in which a relay optic 620 is used between the eye and meta-lens 610. When a relay optic 620 is used, the meta-lens 610 may include an aperture stop and aperture on a front surface of the substrate, as depicted in FIG. 1. The relay optic can relay an image of the eye's pupil onto the meta-lens' input aperture, so that the separation between the pupil and meta-lens does not limit the FOV of the ocular imaging system. The relay optic 620 may be a large spherical, ellipsoidal, or parabolic reflector or a large lens. Relaying the pupil onto the meta-lens' input aperture allows the angle-of-incidence on the meta-lens' aperture to be increased up to nearly ±90°, thus utilizing the full FOV of the meta-lens 610. One implementation of the relay optic 620 can be an ellipsoidal reflector in which the eye pupil and the meta-lens input aperture are positioned at the reflector's two foci, so that light emitted from one point near the first focal point converges to a point near the second focal point. Another implementation of the relay optic 620 is a freeform reflector. Yet another implementation of the relay optic 620 is a meta-surface, diffractive optical elements, holographic optical elements designed to, for example, produce constant optical path lengths between the eye pupil and the meta-lens' input aperture. Yet another implementation of the relay optic 620 is a meta-surface formed on a curved surface, e.g., a reflective meta-surface. An integrated circuit 480 having photodetectors and light-emitting devices can be located at a focal plane 150 of the meta-lens 610 for illumination and image acquisition.

Using a relay optic 620 can allow the meta-lens 610 to be located farther from the eye than in previous embodiments, e.g., up to 200 mm. However, larger effective optical path distances between the eye and meta-lens 610 may require larger-diameter relay optics. For example, at a distance of 200 mm, the diameter of the relay optic may be between 100 mm and 200 mm.

The ocular imaging systems described above may be used in reverse to perform near-eye projection of an image onto the retina. For example, the image sensor (photodetectors) may be replaced or augmented by a light emitter array or micro-display 780, as depicted in the near-eye display system 700 of FIG. 7. The emitter array or micro-display 780 can be used to form images that are projected by the meta-lens 710 over a wide FOV (e.g., between 70° and 200°) onto the retina for user viewing. The emitter array or micro-display 780 may be located within 10 mm from the meta-lens 710, which can be located within 40 mm or within 100 mm of the pupil. FIG. 7 depicts emission from three point sources of an image to simplify the drawing, but in practice emission can be from an extended and continuous image over part or all of the emitter-array or micro-display 780. In some cases, a curved and/or conformal optical system (such as that depicted in FIG. 5C) can be configured for near-eye display and placed in contact with the eye (e.g., by integration into a contact lens). One or more near-eye display systems 700 may be provided for each eye for stereo and/or 3D display.

Additionally or alternatively to direct projection of the image onto the retina, a relay and/or combiner optic can be included to redirect the light emitted from the meta-lens towards the eye, similar to the ocular imaging systems described in connection with FIG. 6. The combiner can combine the projected image with other optical beams. For example, in a see-through configuration in AR systems, the projected image can be combined with the scene of the outside world that would normally be viewed by the user. The relay and/or combiner optics can be in the form of meta-optics, diffractive optical elements, holographic optical elements, beam splitters, refractive or reflective optics, waveguide optics, etc.

In a near-eye display system, the wide FOV meta-lens can readily enable advanced light manipulation emitted towards the eye with high-quality beam shaping, collimation, focusing, steering, and image/pattern projection with high angular resolution. Such functionality, along with aberration-free imaging, is desirable for a variety of applications beyond retinal illumination/imaging, such as AR/VR. The above-described meta-lens based imaging and near-eye display systems (and eye-tracking systems described below) are fully compatible with integration of state-of-the-art micro-LED emitter arrays, micro-displays, and image sensor arrays (now available with less than 3 micron pitch). Such near-eye display systems can have the same form factor, power, and cost advantages of the ocular imaging systems described above. Accordingly, AR and VR systems using meta-lenses can be small, lightweight, and exhibit very large FOVs for user convenience and improved realism.

Meta-lens based optical systems may also be used for eye-tracking applications. Eye-tracking technology can be useful for such applications as human-computer interaction, cognitive science, marketing research, AR/VR, human factors, ergonomics, psycholinguistics, neurological diagnosis, and so on. Eye-tracking technology can be useful for head-mounted displays which may rely on eye movement to realize user interactions.

Eye-tracking systems measure the eyes' gazing point, orientation, and/or position. Video-based, optical eye-tracking systems typically include a light source or a pattern projector that illuminates the eyes with one or more beams (usually in the near-IR) and an imager that images the eyes and the reflected beam or pattern of beams. Information about the eyes' gazing point, orientation, and/or position can be extracted by analyzing the captured image and/or reflected optical signals. For example, the corneal reflection and the center of the pupil can be used as features to determine the gazing point, orientation, and/or position of an eye. Reflections from different eye tissues can also be used as features for tracking, such as the front of the cornea and the back of the lens. Features inside the eye (e.g., retinal blood vessels) can also be used for more precise eye tracking, which may demand a more complex imaging configuration. The eye-tracking implementations described below are well-suited for wearable or head-mounted devices and can be combined with near-eye display systems described above. The combination of the near-eye display and eye-tracking functions using a meta-lens based platform can enable ultra-compact AR/VR systems with a robust, low complexity, thin, and light-weight apparatus having no moving parts.

FIG. 8A depicts an eye-tracking system 800 that includes two meta-lenses 810, 812. The eye-tracking system 800 also includes an emitter 820 and an imager 830. The meta-lenses 810, 812, emitter 820, and imager 830 can be mounted on a frame or substrate 802, which may be the frame of eyeglasses, a transparent lens, screen, or visor, for example, positioned in front of a user's eye. The meta-lenses 810, 812 may be oriented to a same plane or parallel planes. The emitter 820 may include one or more light-emitting devices that emit light (e.g., near-infrared light) toward a first meta-lens 810. The first meta-lens may form one or more beams that are projected onto the eye. The one or more beams may illuminate one or more of the cornea, fundus, retinal blood vessels, pupil, etc.

A second meta-lens 812 may be arranged on an opposite front side of the eye and designed to image light reflected from the eye onto an imager 830. The arrangement of meta-atoms on the second meta-lens may differ from the arrangement of meta-atoms on the first meta-lens 810. The imager can include an array of photodetectors to record electronic images of the eye. The imager 830 may be in communication with a processor (e.g., a microcontroller, digital signal processor, microprocessor, or some combination thereof) so that recorded images of the eye can be processed to track eye movement and determine gazing point, orientation, and/or position of the eye.

FIG. 8B depicts an example of an eye-tracking system 802 in which the functionalities of illumination and imaging are combined onto same substrates (similar to that described above for the ocular imager of FIG. 4). For example, two meta-lenses 840 may have identical arrangements of meta-atoms on their meta-surfaces. Each meta-lens may include an illumination zone 842 and an imaging zone 846. Similarly, each integrated circuit 850 may include an emitter region with light-emitting devices and an imaging region with photodetectors. Each integrated circuit 850 and meta-lens 840 may, in part, project one or more beams onto the eye, and each integrated circuit 850 and meta-lens 840 may, in part, image light reflected from the eye to track eye movement. As with the imager of FIG. 4, in other implementations the functionalities of illuminating and imaging may be spatially overlapped on the meta-lenses 840 and integrated circuits 850.

The eye-tracking optical systems of FIG. 8A and FIG. 8B may be arranged on a curved surface, as depicted in the example of FIG. 8C. For example, the first meta-lens 810, second meta-lens 812, emitter 820, and imager 830 may be mounted in two separated modules that can be oriented tangentially to a spherical surface 870. A curved surface configuration can improve light capturing at large angles, may facilitate system integration, and allow ergonomic designs tailored for human body shapes for applications such as wearable and head mounted devices. In some cases, at least part of the curved and/or conformal eye-tracking system may be placed in contact with the eye, for example, by integration into a contact lens. For example, an emitter 820 and its meta-lens may be integrated into a contact lens, and an imager 830 and its meta-lens may be mounted external to the eye. Alternatively, the imager and its lens may be integrated into a contact lens and the emitter and its lens external to the eye.

For the above-describe eye-tracking systems and display systems, the meta-surface of a meta-lens can be encoded with meta-atoms to allocate different zones for different light-manipulation tasks. Alternatively, a meta-surface can be encoded to multiplex different functional zones and light-manipulation tasks together over a shared region of the meta-lens. Light emitters can be coupled with the illumination zone(s) of a meta-lens to generate two-dimensional or three-dimensional spot arrays and/or illumination patterns on the tissues of interest. In some cases, a single light emitter can be coupled with an illumination zone (e.g., a meta-surface designed as a holograph or spot generator) to generate 2D/3D spot arrays and/or illumination patterns. Light reflected by tissue is coupled by the imaging zone onto the photodetectors to generate electronic images. The meta-lenses of the eye-tracking systems may be located within 40 mm or within 100 mm of the eye's pupil and within 10 mm of the emitter or imager.

For some implementations, the entire meta-surface can be designed to generate and image multiple spot arrays and/or illumination patterns on different tissues or different locations in three-dimensional space and to track them separately. The imaging meta-lens can be designed to capture images at different depths or from different tissues. The meta-surface can also be designed to illuminate and image an object from different angles to generate a 3D image for stereo imaging, for example. Additionally, a meta-surface can be designed to provide wavelength-filtering functionality. For example, amorphous-Si nano-posts can be designed to block light with wavelengths shorter than approximately 650 nm while passing longer wavelengths.

The small form factor of the meta-lens based imagers, near-eye displays, and eye-trackers can allow multiple projection and imaging sub-modules/sub-zones to be integrated at different locations in an ocular device, as is done for the example systems of FIG. 8A, FIG. 8B, and FIG. 8C. Multiple modules may be useful for stereo and/or 3D imaging and projection. Two or more modules may be used for each eye. Each module may include multiple zones for pattern projection and imaging functionalities, as described above.

The above-described wide FOV meta-lenses can be relatively straightforward to fabricate using conventional micro-fabrication technologies. Fabrication methods can include patterning resist and performing lift-off or etching process steps. Example fabrication methods are described in U.S. patent application Ser. No. 16/894,945 titled "Ultra-Wide Field-of-View Flat Optics," filed Jun. 8, 2020, which description of fabrication is incorporated herein by reference. The meta-lenses can be designed to operate at a wide range of wavelengths (e.g., from ultraviolet to microwave frequencies with a bandwidth that spans up to an octave), depending on the selected design and arrangement of meta-atoms and the substrate and meta-atom materials.

Methods of operating a meta-lens based ocular imaging, near-eye display, or eye-tracking system are possible with the above-described embodiments. FIG. 9 depicts acts that may be performed when operating an ocular imaging system, for example. Such a method 900 may include acts of directing (act 910) light from a light-emitting device toward an eye and operating (act 920) on the light with one or more illumination zones of one or more meta-lenses. Operating on the light may comprising collimating, focusing, or patterning the light (e.g., forming a pattern of spots or forming an image) with the one or more illumination zones. The method 900 may further include operating (act 930) on light reflected from eye tissue with one or more imaging zones of one or more meta-lenses. Operating on the reflected light may comprise focusing the light onto sensors (e.g., photodetectors) of one or more integrated circuits located behind the meta-lens(es). The sensors may then be used to record (act 940) an image. The method 900 may further include processing recorded images to detect a physical condition of the eye or to detect movement of the eye (e.g., performing eye-tracking).

Various configurations of meta-lens-based ocular imaging apparatus and methods of operating the imaging apparatus are included as set forth below.

(1) An ocular imaging system comprising: a substrate having a first meta-surface formed thereon, the meta-surface comprising an imaging zone having a first plurality of meta-atoms, wherein the meta-surface is to be positioned within 100 mm of an eye's pupil to image an interior portion of the eye; a light source to illuminate an interior of the eye; and an array of photodetectors located at a focal surface of the meta-surface to detect an image of the interior portion of the eye that is formed by the imaging zone.

(2) The ocular imaging system of configuration (1), wherein the pupil of the eye acts as an aperture stop for the ocular imaging system to obtain high-resolution images.

(3) The ocular imaging system of configuration (1) or (2), further comprising an illumination zone on the substrate formed from a second plurality of meta-atoms, the second plurality of meta-atoms arranged to collimate, focus, or pattern light from the light source onto the eye.

(4) The ocular imaging system of any one of configurations (1) through (3), wherein the light source comprises one or more light-emitting diodes adjacent to the array of photodetectors.

(5) The ocular imaging system of configuration (4), wherein a total thickness of the ocular imaging system is no greater than 20 mm.

(6) The ocular imaging system of configuration (4) or (5), wherein a total volume of the ocular imaging system is no greater than 100 cm3.

(7) The ocular imaging system of any one of configurations (1) through (6), wherein the substrate comprises sapphire, silica, calcium fluoride, or a polymer.

(8) The ocular imaging system of configuration (7), wherein the first plurality of meta-atoms are formed from a dielectric, semiconductor, or metal material.

(9) The ocular imaging system of any one of configurations (1) through (8), wherein the first plurality of meta-atoms comprises meta-atoms of at least two different shapes or sizes that are repeated across the substrate.

(10) The ocular imaging system of any one of configurations (1) through (9), wherein the substrate has at least one curved surface.

(11) The ocular imaging system of configuration (10), wherein the focal surface is curved.

(12) The ocular imaging system of any one of configurations (1) through (11), further comprising: an aperture stop formed on a second surface of the substrate; and a relay optic to relay an image of the pupil of the eye onto an aperture formed by the aperture stop.

The following methods may be used to operate ocular imaging systems of one or more of the above configurations and following configurations.

(13) A method of operating an ocular imaging system, the method comprising: directing light from a light source toward an eye; collimating, focusing, or patterning the light with an illumination zone of a meta-surface, the illumination zone comprising a first plurality of meta-atoms formed on a substrate; focusing light reflected from the eye with an imaging zone of the meta-surface, the imaging zone comprising a second plurality of meta-atoms formed on the substrate; and detecting the focused light with an array of photodetectors.

(14) The method of (13), further comprising using the pupil of the eye as an aperture stop for the ocular imaging system.

(15) The method of (13) or (14), further comprising forming an image of a retina of the eye having a field-of-view that is between 70 degrees and 200 degrees as measured around the interior of the eye.

The following configurations may include one or more features from any one of configurations (1) through (12) above.

(16) A near-eye display system comprising: a substrate having a meta-surface formed thereon, the meta-surface comprising a plurality of meta-atoms, wherein the meta-surface is to be positioned within 100 mm of an eye's pupil; and a micro-emitter array or micro-display located within 10 mm of the meta-surface to form an image that is projected by the meta-surface onto the retina of the eye, wherein the image covers a field-of-view between 70 degrees and 200 degrees as measured around the interior of the eye.

(17) The near-eye display system of configuration (16), wherein the near-eye display system utilizes the pupil as an aperture stop to obtain high resolution image projection.

(18) The near-eye display system of configuration (16) or (17), wherein the substrate is formed of sapphire and the meta-atoms are formed of silicon.

(19) An eye-tracking system comprising: an emitter to produce illumination light; a first meta-surface that is within 10 mm of the emitter and within 40 mm or within 100 mm of an eye's pupil, the first meta-surface including a first plurality of meta-atoms formed on a surface of a first substrate and arranged to project a pattern of the illumination light onto the eye; a second meta-surface located within 40 mm or within 100 mm of the eye's pupil, the second meta-surface including a second plurality of meta-atoms arranged to image a region of the eye illuminated by the pattern; and an imager having a plurality of photodetectors to record an image of the region of the eye.

(20) The eye-tracking system of configuration (19), wherein the second meta-surface is formed on a surface of a second substrate that is separated from the first substrate, and wherein the first meta-surface and the second meta-surface lie in a same planar surface or lie in parallel planar surfaces.

(21) The eye-tracking system of configuration (19), wherein the second meta-surface is formed on a surface of a second substrate that is separated from the first substrate, and wherein the first meta-surface and the second meta-surface lie on a curved surface.

(22) The eye-tracking system of any one of configurations (19) through (21), wherein the second meta-surface is formed on the surface of the first substrate, and wherein the emitter and the imager are located on a same substrate.

While various inventive implementations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive implementations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been described. The acts performed as part of the method may be ordered in any suitable way. Accordingly, implementations may be constructed in which acts are performed in an order different than illustrated, which may include performing some acts simultaneously, even though shown as sequential acts in illustrative implementations.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one implementation, to A only (optionally including elements other than B); in another implementation, to B only (optionally including elements other than A); in yet another implementation, to both A and B (optionally including other elements); etc.

As used herein in the specification and in the claims, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e. “one or the other but not both”) when preceded by terms of exclusivity, such as “either,” “one of,” “only one of,” or “exactly one of.” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one implementation, to at least one, optionally including more than one, A, with no B present (and optionally including elements other than B); in another implementation, to at least one, optionally including more than one, B, with no A present (and optionally including elements other than A); in yet another implementation, to at least one, optionally including more than one, A, and at least one, optionally including more than one, B (and optionally including other elements); etc.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

The invention claimed is:

1. A method of projecting an image or pattern into an eye with a display system that comprises a source of an image or pattern and a meta-surface, the method comprising:

forming an image or pattern projected from the source around an interior portion of an eye with the meta-surface, wherein:

the meta-surface comprises meta-atoms disposed on a substrate;

the image or pattern projected into the eye covers a field-of-view of at least 70 degrees around an interior of the eye; and the meta-atoms comprise:

a plurality of cylindrical pillars disposed on a substrate, wherein the plurality of cylindrical pillars have at least eight different diameters less than the wavelength of light used to form the image or pattern and impart phase delays in a range from at least 50 degrees to 300 degrees to the light.

2. The method of claim 1, further comprising using the pupil of the eye as an aperture stop in the display system.

3. The method of claim 1, wherein the substrate has at least one curved surface.

4. The method of claim 1, wherein the substrate comprises at least one of sapphire, silica, calcium fluoride, chalcogenide, glass, semiconductor, or polymer.

5. The method of claim 4, wherein the meta-atoms are formed from at least one of a dielectric, semiconductor, or metal.

6. The method of claim 1, wherein the meta-atoms comprise meta-atoms of at least two different shapes or sizes that are repeated across the substrate.

7. The method of claim 1, further comprising providing multiplexed optical functions with at least a portion of the meta-atoms located in a same area of the meta-surface.

8. The method of claim 7, wherein providing multiplexed optical functions comprises:

illuminating a first region of the eye or projecting the image or pattern to the eye as a first optical function of the multiplexed optical functions; and forming an image of the first region or of a second region of the eye as a second optical function of the multiplexed optical functions.

9. The method of claim 1, wherein the meta-atoms are first meta-atoms, and further comprising:

receiving, with a meta-optical element having second meta-atoms, optical rays from the meta-surface;

redirecting the optical rays, with the meta-optical element, to participate in forming the image or pattern; and providing multiplexed optical functions with at least some of the second meta-atoms that are located in a same area of a meta-surface of the meta-optical element.

10. The method of claim 1, wherein the source comprises a light emitter, an emitter array or a micro-display.

11. A method of projecting an image or pattern into an eye with a display system that comprises a source of an image or pattern and a meta-surface, the method comprising:

forming an image or pattern projected from the source around an interior portion of an eye with the meta-surface, wherein:

the meta-surface comprises meta-atoms disposed on a substrate, and the image or pattern projected into the eye covers a field-of-view of at least 70 degrees around an interior of the eye;

receiving, with at least one optical element in the display system, optical rays from the meta-surface; and redirecting the optical rays, by the at least one optical element, to participate in forming the image or pattern, wherein the at least one optical element comprises a meta-optic, a diffractive optical element, a holographic optical elements, a beam splitter, a refractive or reflective optic, or a waveguide.

12. The method of claim 11, further comprising:

combining, by the at least one optical element, the image or pattern from the source with other optical beams or a second image or pattern; and projecting a combination of the image or pattern and the other optical beams or the second image or pattern to the eye.

13. A method comprising:

emitting illumination light with an emitter;

projecting, with a first meta-surface located a first distance from a pupil of an eye, a pattern of the illumination light onto the eye, wherein:

the first meta-surface comprises a first plurality of meta-atoms disposed on a surface of a first substrate, and;

the first plurality of meta-atoms comprise:

a plurality of cylindrical pillars disposed on a substrate, wherein the plurality of cylindrical pillars have at least eight different diameters less than the wavelength of the illumination light used to form the pattern and impart phase delays in a range from at least 50 degrees to 300 degrees to the illumination light;

imaging, with a second meta-surface located a second distance from the pupil, a region of the eye illuminated by the pattern, wherein the second meta-surface comprises a second plurality of meta-atoms; and recording an image of the region of the eye.

14. The method of claim 13, wherein a first area occupied by the first plurality of meta-atoms at least partially overlaps a second area occupied by the second plurality of meta-atoms.

15. The method of claim 13, further comprising providing multiplexed optical functions with at least the first plurality of meta-atoms.

16. The method of claim 13, wherein the second meta-surface is formed on a surface of a second substrate that is separated from the first substrate.

17. The method of claim 13, wherein at least the first meta-surface lies on a curved surface.

18. The method of claim 13, further comprising tracking movement of the eye based on at least the image of the region of the eye.

19. The method of claim 13, further comprising determining at least one of a gazing point of the eye, an orientation of the eye, or a position of the eye based on at least the image of the region of the eye.

20. The method of claim 13, wherein the image of the region of the eye comprises an image of at least one of a retina, pupil, palpebral, scleral, pars-planar, or iris of the eye.

* * * * *